United States Patent
Pfrang et al.

(10) Patent No.: US 9,713,683 B2
(45) Date of Patent: Jul. 25, 2017

(54) GRID ELEMENT FOR AN INHALER

(71) Applicant: Gerresheimer Regensburg GmbH, Regensburg (DE)

(72) Inventors: Juergen Pfrang, Kallmuenz (DE); Vaclav Vojan, Plzen (CZ); Udo Leuschner, Regensburg (DE)

(73) Assignee: GERRESHEIMER REGENSBURG GMBH, Regensburg (DE)

( * ) Notice: Subject to any disclaimer, the term of this patent is extended or adjusted under 35 U.S.C. 154(b) by 0 days.

(21) Appl. No.: 15/170,704

(22) Filed: Jun. 1, 2016

(65) Prior Publication Data
US 2016/0354563 A1    Dec. 8, 2016

(30) Foreign Application Priority Data
Jun. 5, 2015 (DE) ................. 10 2015 108 931

(51) Int. Cl.
*A61M 15/00* (2006.01)
*A61M 11/00* (2006.01)

(52) U.S. Cl.
CPC ...... *A61M 15/0005* (2014.02); *A61M 11/003* (2014.02); *A61M 15/00* (2013.01); *A61M 15/003* (2014.02); *A61M 15/0021* (2014.02); *A61M 2206/14* (2013.01); *A61M 2207/00* (2013.01)

(58) Field of Classification Search
CPC ............ A61M 15/0005; A61M 15/003; A61M 15/0021; A61M 2207/00; A61M 2206/14; A61M 15/00; A61M 15/0006; A61M 15/0008; A61M 15/0028; A61M 15/0033; A61M 15/0035; A61M 15/0036; A61M 15/0038; A61M 15/004; A61M 15/0041; A61M 15/0043; A61M 11/003
USPC ...................................... 128/203.12
See application file for complete search history.

(56) References Cited

U.S. PATENT DOCUMENTS

| | | | | |
|---|---|---|---|---|
| 3,888,252 A | * | 6/1975 | Side ................. | A61M 15/0028 128/203.15 |
| 4,995,385 A | * | 2/1991 | Valentini ........... | A61M 15/0028 128/203.15 |
| 6,418,926 B1 | * | 7/2002 | Chawla .................... | A61J 1/00 128/203.12 |
| 9,010,323 B2 | * | 4/2015 | Haerder ............ | A61M 15/0028 128/203.15 |

FOREIGN PATENT DOCUMENTS

GB    WO 2015075433 A1 * 5/2015 .......... A61M 15/003

* cited by examiner

*Primary Examiner* — Kathryn E Ditmer
(74) *Attorney, Agent, or Firm* — Lathrop & Gage LLP

(57) ABSTRACT

The invention relates to a grid element for an inhaler which can be arranged in an air duct between a mouthpiece and a capsule chamber of the inhaler, it being possible for turbulence to be generated by means of the grid element in an airflow passing through the air duct. The grid element is characterized in that it comprises a preferably planar grid-type portion having a grid front side which points towards the capsule chamber and a grid rear side, at least one protruding element being arranged on the grid front side, by means of which a capsule that can be arranged in the capsule chamber can be loosely supported.

20 Claims, 4 Drawing Sheets

GRID ELEMENT FOR AN INHALER

CROSS-REFERENCE TO RELATED APPLICATIONS

This patent application claims the benefit of priority from German application DE 10-2015-108-931.9, filed on Jun. 5, 2015, the contents of which are incorporated herein by reference.

BACKGROUND OF THE INVENTION

The invention relates to a grid element for an inhaler which can be arranged in an air duct between a mouthpiece and a capsule chamber of the inhaler, it being possible for turbulence to be generated by means of the grid element in an airflow passing through the air duct.

In the prior art, several principles according to which inhalers operate are known. The present invention relates to a grid element for inhalers for the inhalation of pulverulent pharmaceutical products from capsules. Such inhalers are also referred to as Bernoulli inhalers and are marketed for example under the name HandiHaler. In this case, the pulverulent active ingredient is stored in a capsule. These capsules are conventionally produced from hard gelatine and consist of two cylindrical parts, the ends of which are in the form of hemispheres. Document DE 198 35 346 A1 discloses for example such a capsule.

Such a capsule is introduced into a generally cylindrical capsule chamber of the inhaler. Said capsule chamber comprises an air inlet at one of the axial ends thereof, and an air outlet duct at another axial end, which air outlet duct extends as far as the mouthpiece. Furthermore, the capsule chamber is dimensioned in such a way that the length and width thereof are greater than the dimensions of the capsule. However, the axial longitudinal axis of the capsule is still arranged substantially in parallel with an axial longitudinal axis of the capsule chamber.

Prior to an inhalation, the capsule must firstly be opened. For this purpose, the inhaler comprises a piercing or cutting device. Said piercing device comprises two needles which are at a distance from one another along an axis which extends in parallel with the axial longitudinal axis of the capsule chamber. The needles are pressed against the capsule by means of an actuation button, as a result of which two openings are produced in the longitudinal outer surface of the capsule. Some capsules comprise corresponding taperings in material at the piercing points.

If air is now sucked through the mouthpiece, an airflow is produced in the capsule chamber from the air inlet to the air outlet duct. By means of the airflow flowing past the openings, a negative pressure is generated in front of the capsule openings with respect to the inside of the capsule, so that the powder which is located in the capsule is carried away by the airflow and atomised in the process. In addition, the capsule vibrates through the airflow predominantly along the axial longitudinal axis. Due to the already-mentioned dimensioning of the capsule chamber, the capsule can vibrate both vertically and horizontally.

Such inhalers are disclosed for example in documents DE 39 27 170 A1, DE 33 45 722 A1 and DE 43 18 455 A1.

In the inhalers mentioned at the outset, a grid or a filter respectively is conventionally arranged between the mouthpiece and the capsule chamber. This grid is used to generate turbulence in the airflow which passes through the air outlet duct. This turbulence assists with deaglommeration of the inhalation powder, as a result of which the active ingredients are better distributed in the aerosol to be breathed in and thus can be better absorbed by the lungs. In addition, such a grid is intended to filter undesirable particles from the capsule chamber out of the inhalation path. Undesirable particles of this type are for example plastics material particles which are produced by means of the abrasion of the needles for opening the capsule on the housing or fragments of the capsule which are produced when opening the capsule. An additional function of the grid is to spatially limit the movement of the capsule in the capsule chamber. The ability of the capsule to move must be limited in such a way that, although it can vibrate both vertically and horizontally in the capsule chamber, in this respect, it still remains oriented substantially in parallel with the axis of the chamber. So that the grid provides a spatial delimitation of this type, it must have a shape which is appropriate for insertion in the inhaler. Such a grid is typically produced by overmoulding a plastics material frame on a metal grid, which frame is then inserted in the inhaler. Such grids are thus expensive and elaborate to produce.

It is thus an object of the invention to provide a grid element for an inhaler which is simple and cost-effective to produce. It is also an object of the present invention to provide an inhaler having such a grid element.

SUMMARY OF THE INVENTION

This object is achieved by a grid element for an inhaler which can be arranged in an air duct between a mouthpiece and a capsule chamber of the inhaler, it being possible for turbulence to be generated by means of the grid element in an airflow passing through the air duct. The grid element is characterised in that it comprises a preferably planar grid-type portion having a grid front side which points towards the capsule chamber and a grid rear side which points towards the mouthpiece, at least one protruding element being arranged on the grid front side, by means of which a capsule that can be arranged in the capsule chamber can be loosely contacted.

Being able to be loosely contacted is to be understood to mean that the capsule is to be held only to the extent to which it can vibrate both vertically and horizontally in the capsule chamber, but in this respect remains oriented substantially in parallel with the axis of the chamber.

Owing to such a design of a grid element, said element can be formed as desired. The grid element must merely be able to be arranged in the inhalation path in the region between the inhalation capsule and the upper airway of the patient in order to generate turbulence in the airflow. The precise position of the arrangement of the grid element is no longer determined by the requirement to limit the ability of the capsule to move. Instead, the grid element can be arranged in the mentioned region as desired. Only a corresponding adaptation of the element protruding on the grid front side is required. Such an adaptation is easy to carry out in production. Furthermore, the grid element is preferably arranged in the region of the mouthpiece.

Preferably, only one protruding element, which preferably extends substantially in a normal direction of the grid-type portion, is arranged centrally on the grid front side. Owing to the central arrangement, the capsule can be held loosely in the capsule chamber in a simple manner.

According to a preferred aspect of the invention, the grid webs forming the grid-type portion have a height that extends in the normal direction, the grid-type portion comprising at least one region in which said height is increased in the normal direction, by means of which the protruding element is formed. Such a design of the grid element has the advantage that said element can be produced in a particularly simple manner, since the protruding element is integral with the grid-type portion and thus does not have to be additionally arranged on the grid front side. Preferably, the intersecting grid webs enclose a right angle. However, other grid patterns, for example a diamond pattern, are also conceivable.

According to a particularly preferred embodiment, two grid webs intersect the centre of the grid-type portion. Said two grid webs comprise a portion which intersects the centre, and the height of which is increased in the normal direction. The protruding element is thus in the form of a cross-like protrusion. A cross-like design of this type of the protruding element allows the capsule to be held loosely, and at the same time, the airflow penetrating the grid is not additionally decelerated. The user thus does not have to apply any additional suction.

Preferably, the cross-like protrusion comprises a central portion which is located in a plane which is parallel to a grid surface of the grid front side, the flanks of the cross-like protrusion, proceeding from said central portion, sloping down towards a grid surface of the grid front side. The slope of the flanks preferably defines a second-order curve at least in part. A second-order curve or conic section of this type can be a parabola, circle or an ellipse. Such a design is advantageous, since there are no edges to cause unintentional damage to the capsule. Alternatively, it would be conceivable for the slope of the flanks to be in the form of a straight-lined slope or to have another curved shape. It would likewise be conceivable for the flanks to initially extend in parallel with the grid surface and then extend at a right angle to the grid surface.

However, other embodiments of the protruding element are also conceivable. It would be conceivable to design the protruding element so as to be a hemispherical or rod-shaped body, or in the form of any other desired three-dimensional body. Furthermore, it would also be conceivable to arrange the protruding element in other positions, that is to say eccentrically, on the grid front side. It would also be conceivable to arrange a plurality of protruding elements having the same or different shapes on the grid front side. Lastly, it would also be possible for the protruding element to be made of a different material from the grid, as a result of which the protruding element would have to be attached to the grid element after the production thereof.

According to another advantageous aspect of the invention, the grid element and the grid-type portion are designed to be at least substantially circular. Preferably, in this respect, the grid element comprises an edge region which surrounds the grid-type portion. As a result, the diameter of the grid element is greater than the diameter of the grid-type portion.

Preferably, a front surface of the edge region ends in a planar manner with the grid surface of the grid front side of the grid-type portion, the edge region having a height which is greater than the height of the grid-type portion.

According to another preferred embodiment, a connecting portion is arranged on a rear side of the edge region which, proceeding from the rear side of the edge region, extends in the normal direction with a height. Advantageously, such a connecting portion is designed in such a way that it can be arranged in the air duct of the inhaler between the mouthpiece and the capsule chamber. In this case, the connecting portion can preferably be made of the same material as the edge region and the grid element respectively. In particular, the connecting portion and the edge portion can preferably be integrally formed. However, it would also be conceivable to produce the connecting portion from another material. It would also be conceivable for said material to be a resilient material or an elastomer respectively.

Preferably, the connecting portion is in the form of a hollow right circular cylinder. Preferably, in this case, an inner diameter of the connecting portion corresponds to a diameter of the grid-type portion. More preferably, an outer diameter of the connecting portion is smaller than a diameter of the grid element.

Preferably, a circumferential annular protrusion is arranged on an outer surface of the connecting portion. An annular protrusion of this type can be made of the same material as the grid element. However, it is also conceivable for said annular protrusion to be made of another material. Preferably, said material could be a resilient material, for example an elastomer. It would also be conceivable for a circumferential recess or a groove respectively to be provided on the outer surface, in which a sealing ring or O-ring can be inserted. Advantageously, the air duct in which the grid element is arranged has a design which is complementary to the annular protrusion, for example a recess. A stable connection can thus be ensured, as a result of which only a small amount of undesirable air, that is to say air which has not passed through the capsule chamber, is sucked in.

The grid element is preferably made of a plastics material. More preferably, the grid element can further be produced by means of an injection moulding process. Grid elements of this type are cost-effective to produce in large numbers and with great precision.

The object of the invention is also achieved in another aspect by an inhaler comprising a means having a grid element according to any of the preceding embodiments.

Further advantages, aims and properties of the present invention will be described in greater detail below with reference to the following description of the accompanying drawings. Like components can have the same reference numbers in the different embodiments.

DETAILED DESCRIPTION OF THE INVENTION

Figure 1:
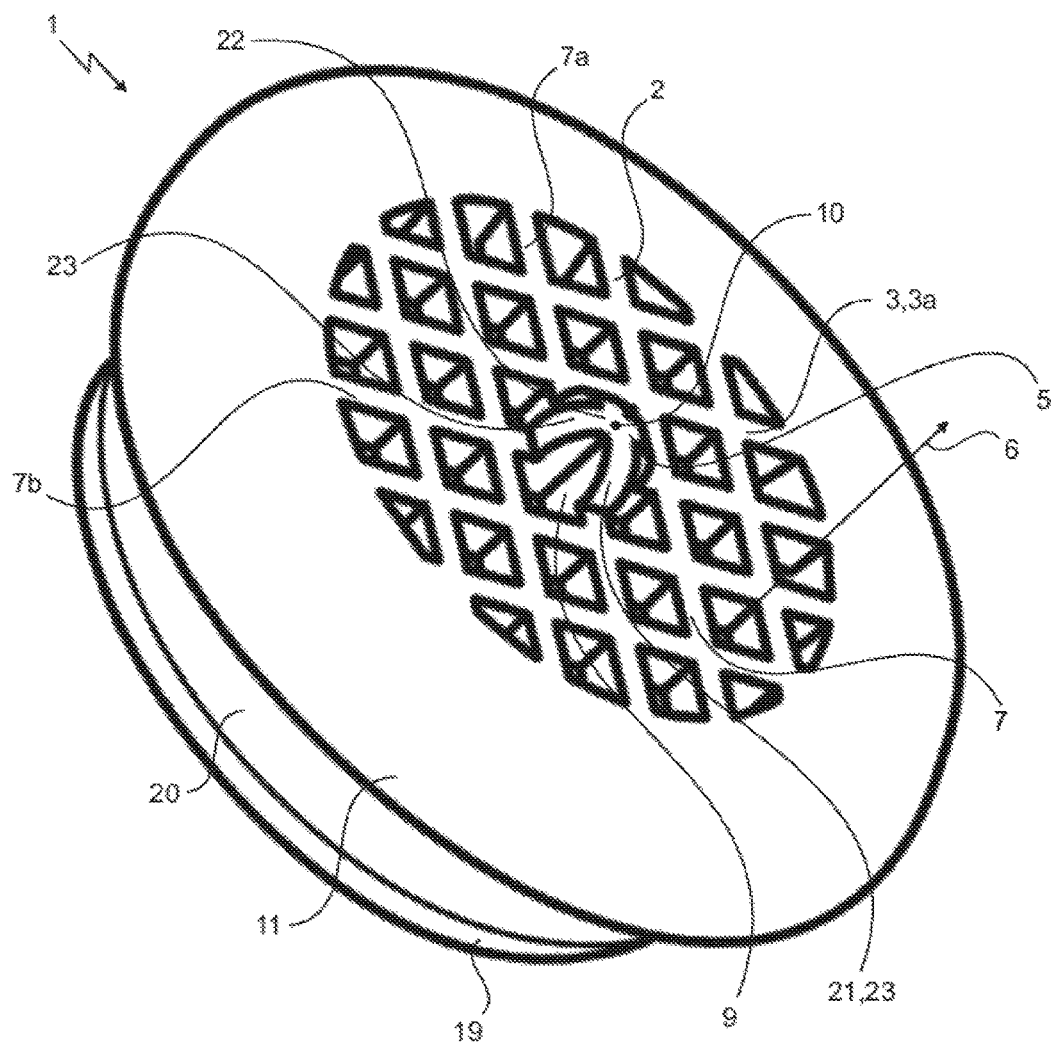
FIG. 1 shows an isometric view of a grid element for an inhaler.
Figure 2:
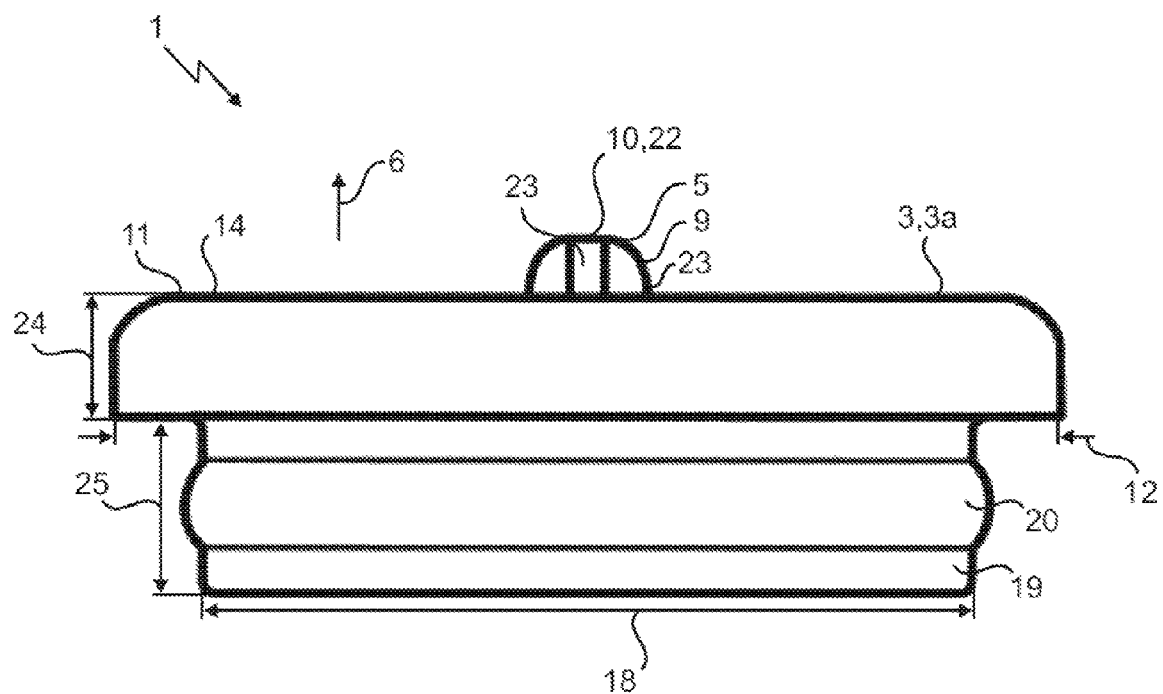
FIG. 2 shows a side view of a grid element for an inhaler.
Figure 3:
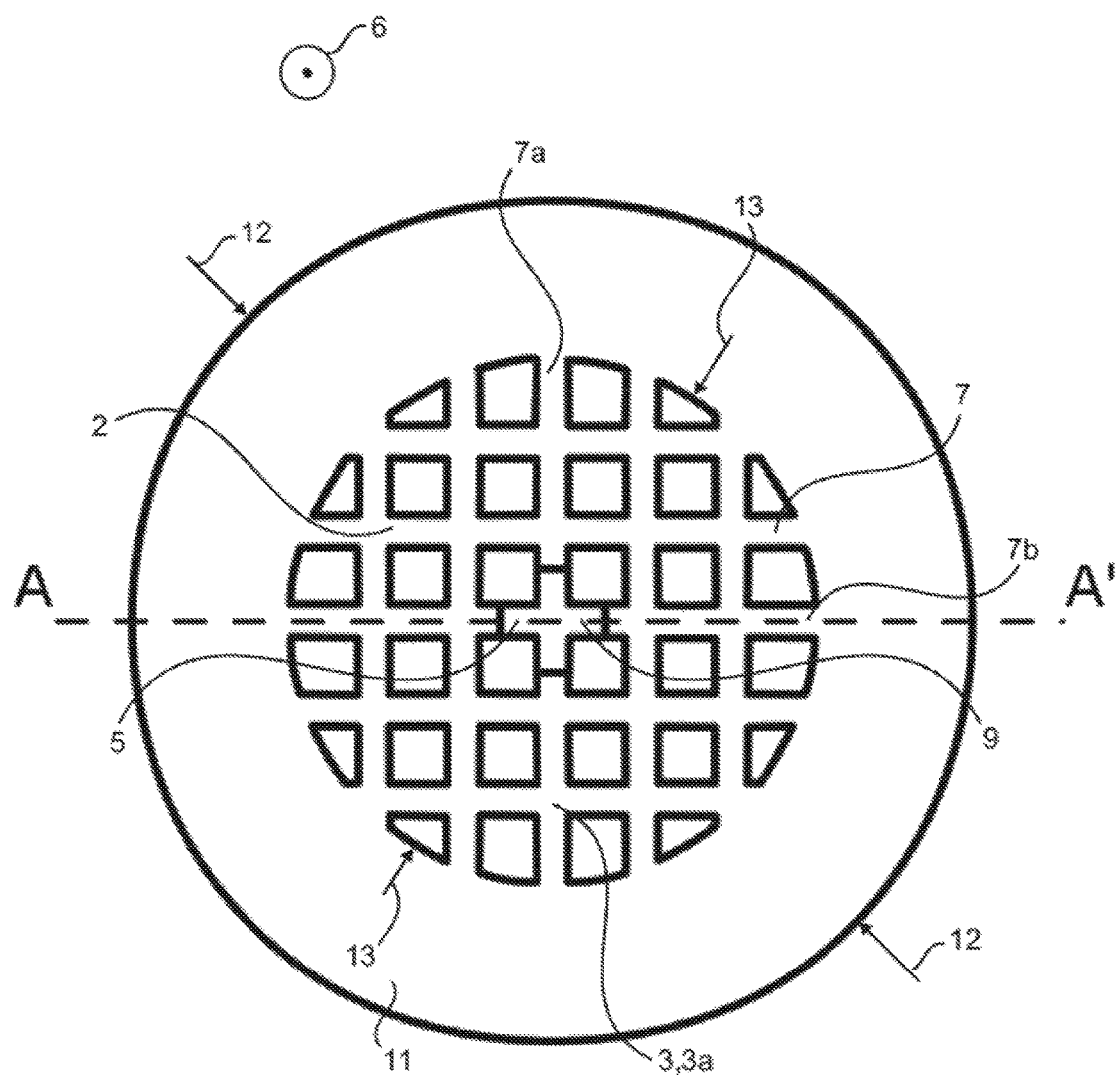
FIG. 3 shows a plan view of a grid element for an inhaler.
Figure 4:
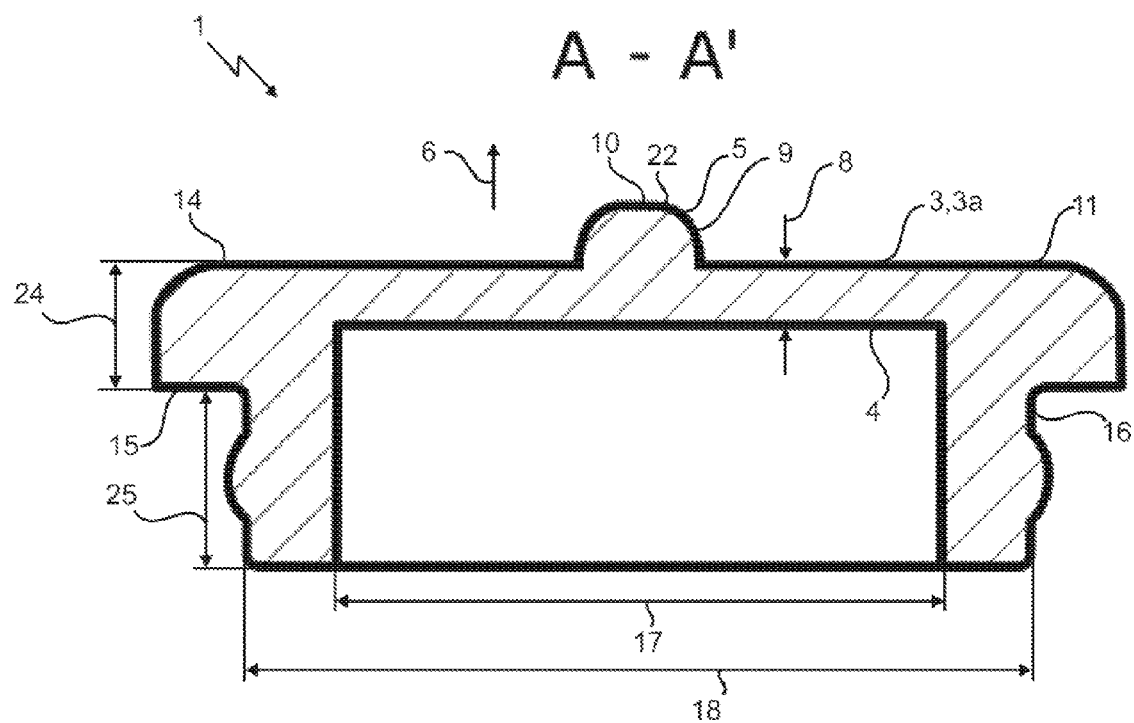
FIG. 4 shows a sectional view of a grid element for an inhaler.

FIGS. 1 to 4 show a grid element (1) for an inhaler. In FIG. 1, this grid element is shown in an isometric view. FIG. 2 shows the grid element in a side view, and FIG. 3 in a plan view. FIG. 3 further shows an intersecting axis A-A'. FIG. 4 lastly shows a corresponding sectional view of the grid element (1) along said intersecting axis (A-A').

The grid element (1) can be arranged in an air duct between a mouthpiece and a capsule chamber of the inhaler, it being possible for turbulence to be generated by means of the grid element (1) in an airflow passing through the air duct. Furthermore, the grid element (1) comprises a preferably planar grid-type portion (2) having a grid front side (3) which points towards the capsule chamber (3) and a grid rear side (4) which points towards the mouthpiece (not shown in FIG. 1). A protruding element (5) is arranged on the grid front side (3). By means of a protruding element (5) of this type, a capsule that can be arranged in the capsule chamber can be loosely contacted. This protruding element (5) is arranged centrally on the grid-type portion (2).

The grid-type portion is formed by grid webs (7) which intersect one another at a right angle. As a result, right-angled grid openings are formed in the grid-type portion (2). The grid webs (7) have a height (8) that extends in the normal direction (6). In this embodiment, the protruding element (5) is formed by a region (9) of the grid-type portion (2) in which the height (8) is increased in the normal direction (6). In particular, this region (9) comprises only the two grid webs (7a, 7b) which intersect a centre (10) of the grid-type portion (2). Said two grid webs (7a, 7b) further comprise a portion in which the height (8) thereof is increased in the normal direction (6). A cross-like protrusion (21) is thus formed on the grid-type portion (2). This cross-like protrusion (21) comprises a central portion (22) which is located in a plane which is parallel to a grid surface (3a) of the grid front side (3). The flanks (23) of the cross-like protrusion (21), proceeding from said central portion (22), slope down towards a grid surface (3a) of the grid front side (3). The slope of the flanks (23) in this case defines a second-order curve at least in part.

In particular FIGS. 1 and 4 show the grid element (1) and the grid-type portion (2) which are designed to be at least substantially circular. The diameter (12) of the grid element (1) in this case is greater than the diameter (13) of the grid-type portion (2). The grid element (1) further comprises an edge region (11) which surrounds the grid-type portion (2).

The edge region (11) comprises a surface (14) which ends in a planar manner with the grid surface (3a) of the grid front side (3) of the grid-type portion (2). In this embodiment, the edges which limit the edge region are rounded. The edge region further has a height (24) which is greater than the height (8) of the grid-type portion (2).

The edge region (11) further comprises a connecting portion (16) on a rear side (15). Said connecting portion (16) extends, proceeding from the rear side (15) of the edge region (11), in the normal direction (6) with a height (25). In this embodiment, the edge region (11) and the connecting portion (16) are integrally formed. The connecting portion (16) is further designed in the form of a circular hollow cylinder. This hollow right circular cylinder has an inner diameter (17) which corresponds to an outer diameter (13) of the grid-type portion (2). Furthermore, the hollow right circular cylinder has an outer diameter (18) which is smaller than the outer diameter (12) of the grid element (1). The edge region (11) and the connecting portion (16) thus form an L-shaped profile in section. This can be seen in FIG. 4. The rear side (15) of the edge region (11) thus forms an edge which protrudes over the connecting portion (16). This is advantageous, since the grid element (1) can thus be attached to the air duct without producing leaks and causing additional suction of undesirable air into the air duct.

The hollow cylindrical connecting portion (16) further comprises an outer surface (19). A circumferential, annular protrusion (20) is arranged on said outer surface (19). Said annular protrusion (20) can be formed integrally with the connecting portion (16) or can be an additionally attached, for example resilient element. In this embodiment, the annular protrusion (20) is arranged centrally with respect to the height (25) and has a round shape which curves radially outwards. This can be seen in FIGS. 2 and 4.

All of the features disclosed in the application documents are claimed as being essential to the invention, whether they are novel individually or in combination over the prior art.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Headings are used herein for convenience only.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. In the disclosure and the claims, "and/or" means additionally or alternatively. Moreover, any use of a term in the singular also encompasses plural forms.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE NUMERALS 1 grid element
2 grid-type portion
3 grid front side
3a grid surface
4 grid rear side
5 protruding element
6 normal direction
7 the grid webs forming the grid-type portion
7a, 7b grid webs which intersect a centre of the grid-type portion
8 height of the grid webs
9 region having an extended height
10 centre of the grid-type portion
11 edge region
12 diameter of the grid element
13 diameter of the grid-type portion
14 surface of the edge region 15 rear side of the edge region
16 connecting portion
17 inner diameter of the connecting portion
18 outer diameter of the connecting portion
19 outer surface of the connecting portion
20 annular protrusion
21 cross-like protrusion
22 central portion of the cross-like protrusion
23 flanks of the cross-like protrusion
24 height of the edge region
25 height of the connecting portion

We claim:

1. A grid element for an inhaler arranged in an air duct between a mouthpiece and a capsule chamber of the inhaler, wherein turbulence is able to be generated by means of the grid element in airflow passing through the air duct, wherein the grid element comprises:
 a planar grid-type portion having a grid front side which points towards the capsule chamber and a grid rear side which points towards the mouthpiece, and
 at least one protruding element being arranged on the grid front side, by means of which a capsule arranged in the capsule chamber can be loosely contacted,
 wherein the protruding element is in the form of a cross-like protrusion comprising a central portion which is located in a plane which is parallel to a grid surface of the grid front side, wherein flanks of the cross-like protrusion, proceeding from said central portion, slope down towards the grid surface of the grid front side, the slope of the flanks defining a second-order curve at least in part.

2. The grid element of claim 1, wherein grid webs forming the grid-type portion have a height that extends in a normal direction, the grid-type portion comprising at least one region in which said height is increased in the normal direction, by means of which the protruding element is formed.

3. The grid element of claim 2, wherein two grid webs intersect a centre of the grid-type portion and comprise a portion which intersects the centre, and the height of which portion is increased in the normal direction.

4. The grid element of claim 1, wherein the grid element and the grid-type portion are designed to be at least substantially circular, the grid element comprising an edge region which surrounds the grid-type portion, and wherein the diameter of the grid element is greater than the diameter of the grid-type portion.

5. The grid element of claim 4, wherein a front surface of the edge region ends in a planar manner with the grid surface of the grid front side of the grid-type portion, the edge region having a height which is greater than the height of the grid-type portion.

6. The grid element of claim 4, wherein, on a rear side of the edge region, a connecting portion is arranged, which extends, proceeding from the rear side of the edge region, in the normal direction with a height.

7. The grid element of claim 6, wherein the connecting portion is in the form of a hollow right circular cylinder, an inner diameter of the connecting portion corresponding to an outer diameter of the grid-type portion, and an outer diameter of the connecting portion being smaller than a diameter of the grid element.

8. The grid element of claim 7, wherein a circumferential, annular protrusion is arranged on an outer surface of the connecting portion.

9. The grid element of claim 1, wherein said grid element consists of a plastics material.

10. The grid element of claim 1, wherein said grid element is produced by means of an injection moulding process.

11. An inhaler comprising a mouthpiece, a capsule chamber, an air duct between the mouthpiece and capsule chamber, and a grid element, said grid element comprising:
 a planar grid-type portion having a grid front side which points towards the capsule chamber and a grid rear side which points towards the mouthpiece, and
 at least one protruding element being arranged on the grid front side, by means of which a capsule arranged in the capsule chamber can be loosely contacted,
 wherein the protruding element is in the form of a cross-like protrusion comprising a central portion which is located in a plane which is parallel to a grid surface of the grid front side, wherein flanks of the cross-like protrusion, proceeding from said central portion, slope down towards the grid surface of the grid front side, the slope of the flanks defining a second-order curve at least in part.

12. The inhaler of claim 11, wherein grid webs forming the grid-type portion have a height that extends in a normal direction, the grid-type portion comprising at least one region in which said height is increased in the normal direction, by means of which the protruding element is formed.

13. The inhaler of claim 12, wherein two grid webs intersect a centre of the grid-type portion and comprise a portion which intersects the centre, and the height of which portion is increased in the normal direction.

14. The inhaler of claim 11, wherein the grid element and the grid-type portion are designed to be at least substantially circular, the grid element comprising an edge region which surrounds the grid-type portion, and wherein the diameter of the grid element is greater than the diameter of the grid-type portion.

15. The inhaler of claim 14, wherein a front surface of the edge region ends in a planar manner with the grid surface of the grid front side of the grid-type portion, the edge region having a height which is greater than the height of the grid-type portion.

16. The inhaler of claim 14, wherein, on a rear side of the edge region, a connecting portion is arranged, which extends, proceeding from the rear side of the edge region, in the normal direction with a height.

17. The inhaler of claim 16, wherein the connecting portion is in the form of a hollow right circular cylinder, an inner diameter of the connecting portion corresponding to an outer diameter of the grid-type portion, and an outer diameter of the connecting portion being smaller than a diameter of the grid element.

18. The inhaler of claim 17, wherein a circumferential, annular protrusion is arranged on an outer surface of the connecting portion.

19. The inhaler of claim 11, wherein said grid element consists of a plastics material.

20. The inhaler of claim 11, wherein said grid element is produced by means of an injection moulding process.

* * * * *